United States Patent
Takeuchi et al.

(10) Patent No.: US 8,440,698 B2
(45) Date of Patent: May 14, 2013

(54) 3-(4-((1H-IMIDAZOL-1-YL)METHYL)PHENYL)-5-ARYL-1,2,4-OXADIAZOLE DERIVATIVES AS SPHINGOSINE-1 PHOSPHATE RECEPTORS MODULATORS

(75) Inventors: Janet A. Takeuchi, Anaheim, CA (US); Ken Chow, Newport Coast, CA (US); Ling Li, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/567,654

(22) Filed: Aug. 6, 2012

(65) Prior Publication Data

US 2012/0302606 A1 Nov. 29, 2012

Related U.S. Application Data

(62) Division of application No. 13/085,868, filed on Apr. 13, 2011, now Pat. No. 8,318,783.

(60) Provisional application No. 61/328,395, filed on Apr. 27, 2010.

(51) Int. Cl.
A61K 31/4245 (2006.01)
A61K 31/454 (2006.01)

(52) U.S. Cl.
USPC ............ 514/326; 514/364; 546/209; 548/131

(58) Field of Classification Search .................. 514/131, 514/311.1; 548/364, 402
See application file for complete search history.

(56) References Cited

FOREIGN PATENT DOCUMENTS

| EP | 2 014 653 A1 | 1/2009 |
|---|---|---|
| WO | WO2006131336 | 12/2006 |
| WO | WO2008037476 | 4/2008 |
| WO | WO 2009 043890 | 9/2009 |
| WO | WO20091561621 | 12/2009 |

OTHER PUBLICATIONS

Schafer et al. Drug Discovery Today, 2008, 13 (21/22), 913-916.*
Horig et al. Journal of Translational Medicine 2004, 2(44).*
P Heinrich Stahl, "Handbook of Pharmaceutical alts Properties, Selection, and Use", 2002. pp. 329-345.
Collators: L. C. Cross, "Rules for the Nomenclature of Organic Chemistry Section E: Stereochemistry", International Union of Pure and Applied Chemistry Organic Chemistry Division Commission on Nomenclature of Organic Chemistry, vol. 45, 1976, pp. 11-13.
Jeffrey J. Hale, "Potent S1P receptor agonists replicate the pharmacologic actions of the novel immune modulator FTY720", Bioorganic & Medicinal Chemistry Letters 14 (2004) 3351-3355.
Emerson Meyer, "Synthesis of New 1,2,4- and 1,3,4-Oxadiazole Derivatives", Departamento de Qufmica, Universidade Federal de Santa Catarina, Florian6polis, SC-88040-900, Brazil, 2003.
Osyanin et al., Russian Journal of General Chemistry, (2005), vol. 75(1), p. 111-117.
Suzanne Mandala et al., Alteration of Lymphocyte Trafficking by Sphingosine-1-Phosphate Receptor Agonists, Science, Apr. 12, 2002, pp. 346-349, vol. 296, American Association for the Advancement of Scient, Washington, DC.
Voler Brinkmann et al., Fingolimod (FTY720): Discovery and Development of an Oral Drug to Treat Multiple Sclerosis, Nature Reviews, Nov. 2010, pp. 883-897, vol. 9, Macmillan Publishers Limited.
Mehrdad Matloubian et al., Lymphocyte Egress from Thymus and Peripheral Lymphoid Organs is Dependent on S1P Receptor 1, Jan. 22, 2004, pp. 355-360, vol. 427, Nature Publishing Group.

* cited by examiner

*Primary Examiner* — Yong Chu
(74) *Attorney, Agent, or Firm* — John E. Wurst; Doina G. Ene; Allergan, Inc.

(57) ABSTRACT

Substituted 3-(4-((1H-imidazol-1-yl)methyl)phenyl)-5-phenyl-1,2,4-oxadiazole derivatives which are useful as sphingosine-1-phosphate modulators and useful for treating a wide variety of disorders associated with modulation of sphingosine-1-phosphate receptors.

8 Claims, 2 Drawing Sheets

3-(4-((1H-IMIDAZOL-1-YL)METHYL)PHENYL)-5-ARYL-1,2,4-OXADIAZOLE DERIVATIVES AS SPHINGOSINE-1 PHOSPHATE RECEPTORS MODULATORS

RELATED APPLICATIONS

This application is a Divisional of U.S. patent application Ser. No. 13/085,868, filed Apr. 13, 2011 now U.S. Pat. No. 8,318,783, which claims the benefit of claims priority under 35 U.S.C. §119(e) to U.S. Provisional Application No. 61/328,395, filed on Apr. 27, 2010, each of which is incorporated herein by reference.

FIELD OF THE INVENTION

The present invention relates to chemical compounds as receptor modulators with therapeutic utility. These compounds may be used as modulators of sphingosine-1-phosphate receptors. The invention relates specifically to the use of these compounds and pharmaceutical compositions to treat disorders associated with sphingosine-1-phosphate (S1P) receptor modulation.

BACKGROUND OF THE INVENTION

Sphingosine is a compound having the chemical structure shown in the structure below. It is known that various sphingolipids, having sphingosine as a constituent, are widely distributed in the living body including on the surface of cell membranes of cells in the nervous system.

sphingosine

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomyeline cycle (in animal's cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Published International Patent Application No. WO 2008037476 describes generically oxadiazoles derivatives with anti-inflammatory and immunosuppressive properties.

Published International Patent Application No. WO 2006131336 describes generically polycyclic oxadiazoles or isoxazoles as S1P receptor ligands.

Published International Patent Application No. WO 2009151621 describes substituted (1,2,4-oxadiazol-3-yl) indolin-1-yl carboxylic acid derivatives useful as S1P1 agonists.

The synthesis of new 1,2,4- and 1,3,4-oxadiazole derivatives structurally related to non-peptide angiotensin II (AII) receptor antagonists is described in Synthesis (2003) issue 6, pages 899-905.

SUMMARY OF THE INVENTION

The invention provides certain well-defined compounds that are useful as sphingosine-1-phosphate modulators. As such, the compounds described herein are useful in treating a wide variety of disorders associated with modulation of sphingosine-1-phosphate receptors. The compounds of the present invention are novel compounds which are potent and selective sphingosine-1-phosphate modulators. The term "modulator" as used herein, includes but is not limited to: receptor agonist, antagonist, inverse agonist, inverse antagonist, partial agonist, partial antagonist.

The present invention describes novel substituted 3-(4-((1H-imidazol-1-yl)methyl)phenyl)-5-phenyl-1,2,4-oxadiazole derivatives as S1P receptors modulators.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

Formula I wherein:

R is H, $O_{1-10}$ alkyl, $O_{3-10}$ cycloalkyl, —$OR^6$, $NR^7R^8$, halogen, nitrile, nitrogen dioxide, $C(O)R^9$, aryl or heterocycle;

$R^1$ is H, $C_{1-10}$ alkyl, $C_{3-10}$ cycloalkyl, —$OR^{10}$, $NR^{11}R^{12}$, halogen, nitrile, nitrogen dioxide, $C(O)R^{13}$, aryl or heterocycle;

$R^2$ is H, $C_{1-10}$ alkyl, halogen, aryl or heterocycle;

$R^3$ is $C_{1-10}$ alkyl, $C_{3-10}$ cycloalkyl, —$OR^{14}$, $NR^{15}R^{16}$, halogen, nitrile, nitrogen dioxide, $C(O)R^{17}$, aryl or heterocycle;

$R^4$ is $C_{1-10}$ alkyl, $C_{3-10}$ cycloalkyl, —$OR^{18}$, $NR^{19}R^{20}$, halogen, nitrile, nitrogen dioxide, $C(O)R^{21}$, aryl or heterocycle;

$R^5$ is $C_{1-10}$ alkyl, $C_{3-10}$ cycloalkyl, —$OR^{22}$, $NR^{23}R^{24}$, halogen, nitrile, nitrogen dioxide, $C(O)R^{25}$, aryl or heterocycle;

a is 0, 1, 2 or 3;
b is 0, 1, 2 or 3;
c is 0, 1, 2 or 3;
$R^6$ is H, $C_{3-10}$ cycloalkyl or $C_{1-10}$ alkyl;
$R^7$ is H or $C_{1-10}$ alkyl;
$R^8$ is H or $C_{1-10}$ alkyl;
$R^9$ is H, $C_{3-10}$ cycloalkyl, —OH, —$OC_{3-10}$ cycloalkyl, —$OC_{1-10}$ alkyl or $C_{1-10}$ alkyl;
$R^{10}$ is H, $C_{3-10}$ cycloalkyl or $C_{1-10}$ alkyl;

$R^{11}$ is H or $C_{1-10}$ alkyl;
$R^{12}$ is H or $C_{1-10}$ alkyl;
$R^{13}$ is H, $C_{3-10}$ cycloalkyl, —OH, —$OC_{3-10}$ cycloalkyl, —$OC_{1-10}$ alkyl or $C_{1-10}$ alkyl;
$R^{14}$ is H, $C_{3-10}$ cycloalkyl or $C_{1-10}$ alkyl;
$R^{15}$ is H or $C_{1-10}$ alkyl;
$R^{16}$ is H or $C_{1-10}$ alkyl;
$R^{17}$ is H, $C_{3-10}$ cycloalkyl, —OH, —$OC_{3-10}$ cycloalkyl, —$OC_{1-10}$ alkyl or $C_{1-10}$ alkyl;
$R^{18}$ is H, $C_{3-10}$ cycloalkyl or $C_{1-10}$ alkyl;
$R^{19}$ is H or $C_{1-10}$ alkyl;
$R^{20}$ is H or $C_{1-10}$ alkyl;
$R^{21}$ is H, $C_{3-10}$ cycloalkyl, —OH, —$OC_{3-10}$ cycloalkyl, —$OC_{1-10}$ alkyl or $C_{1-10}$ alkyl;
$R^{22}$ is H, $C_{3-10}$ cycloalkyl or $C_{1-10}$ alkyl;
$R^{23}$ is H or $C_{1-10}$ alkyl;
$R^{24}$ is H or $C_{1-10}$ alkyl; and
$R^{25}$ is H, $C_{3-10}$ cycloalkyl, —OH, —$OC_{3-10}$ cycloalkyl, —$OC_{1-10}$ alkyl or $C_{1-10}$ alkyl.

The term "alkyl", as used herein, refers to saturated, monovalent or divalent hydrocarbon moieties having linear or branched moieties or combinations thereof and containing 1 to 10 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-10}$ cycloalkyl. Alkyl groups can be substituted by halogen, hydroxyl, cycloalkyl, amino, heterocycles, carboxylic acid, phosphonic acid groups, sulphonic acid groups, phosphoric acid. Usually, in the present case, alkyl groups are methyl, isopropyl, isobutyl, trifluoromethyl.

The term "cycloalkyl", as used herein, refers to a monovalent or divalent group of 3 to 10 carbon atoms, preferably 3 to 5 carbon atoms derived from a saturated cyclic hydrocarbon. Cycloalkyl groups can be monocyclic or polycyclic. Cycloalkyl can be substituted by $C_{1-3}$ alkyl groups or halogens. Usually, in the present case, cycloalkyl groups are cyclopropyl and cyclohexyl.

The term "halogen", as used herein, refers to an atom of chlorine, bromine, fluorine, iodine. Usually, in the present case, halogen groups are chlorine, bromine.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, $C_{1-3}$ alkyl or halogens. Usually, in the present case, heterocyclic groups are oxadiazol, imidazol, 2-methylpiperidine.

The term "aryl" as used herein, refers to an organic moiety derived from an aromatic hydrocarbon consisting of a ring containing 6 to 10 carbon atoms by removal of one hydrogen, which can be substituted by halogen atoms, —$OC_{1-3}$ alkyl, $C_{1-3}$ alkyl, nitrile, $C(O)C_{1-3}$ alkyl, amino or hydroxyl groups. Usually, in the present case, aryl is phenyl.

The term "hydroxyl" as used herein, represents a group of formula "—OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "nitrile", as used herein, represents a group of formula "—CN".

The term "nitrogen dioxide", as used herein, represents a group of formula "—NO$_2$".

The term "sulfoxide" as used herein, represents a group of formula "—S(O)".

The term "carbonyl" as used herein, represents a group of formula "—C(O)".

The term "carboxyl" as used herein, represents a group of formula "—(CO)O—".

The term "sulfonyl" as used herein, represents a group of formula "—SO$_2$".

The term "amino" as used herein, represents a group of formula "—NR$^7$R$^8$".

The term "carboxylic acid" as used herein, represents a group of formula "—COOH".

The term "phosphonic acid" as used herein, represents a group of formula "—P(O)(OH)$_2$".

The term "sulphonic acid" as used herein, represents a group of formula "—SO$_2$(OH)".

The term "phosphoric acid" as used herein, represents a group of formula "—OP(O)(OH)$_2$".

Generally, R is selected from H, $C_{1-10}$ alkyl, $C_{3-10}$ cycloalkyl, —OR$^6$, NR$^7$R$^8$, halogen, nitrile, nitrogen dioxide, C(O)R$^9$, aryl or heterocycle. Usually R is H, nitrile, $C_{1-10}$ alkyl, halogen or nitrogen dioxide. Preferably R is H, nitrile, bromine, trifluoromethyl, nitrogen dioxide, methyl or chlorine.

Generally R$^1$ is selected from H, $C_{1-10}$ alkyl, $C_{3-10}$ cycloalkyl, —OR$^{10}$, NR$^{11}$R$^{12}$, halogen, nitrile, nitrogen dioxide, C(O)R$^{13}$, aryl or heterocycle. Usually R$^1$ is $C_{1-10}$ alkyl, OR$^{10}$, or heterocycle. Preferably R$^1$ is isopropoxy, cyclopropoxy, isobutoxy or 2-methylpiperdin-1-yl.

Generally R$^2$ is selected from H, $C_{1-10}$ alkyl, halogen, aryl or heterocycle. Usually R$^2$ is H, halogen, $C_{1-10}$ alkyl. Preferably R$^2$ is H, methyl, trifluoromethyl or chlorine.

Generally R$^3$ is selected from $C_{1-10}$ alkyl, $C_{3-10}$ cycloalkyl, —OR$^{14}$, NR$^{15}$R$^{16}$, halogen, nitrile, nitrogen dioxide, C(O)R$^{17}$, aryl or heterocycle.

Generally R$^4$ is selected from $C_{1-10}$ alkyl, $C_{3-10}$ cycloalkyl, —OR$^{18}$, NR$^{19}$R$^{20}$, halogen, nitrile, nitrogen dioxide, C(O)R$^{21}$, aryl or heterocycle.

Generally R$^5$ is selected from $C_{1-10}$ alkyl, $C_{3-10}$ cycloalkyl, —OR$^{22}$, NR$^{23}$R$^{24}$, halogen, nitrile, nitrogen dioxide, C(O)R$^{25}$, aryl or heterocycle.

Generally R$^6$ is selected from H, $C_{3-10}$ cycloalkyl or $C_{1-10}$ alkyl.

Generally R$^7$ is selected from H or $C_{1-10}$ alkyl.

Generally R$^8$ is selected from H or $C_{1-10}$ alkyl.

Generally R$^9$ is selected from H, $C_{3-10}$ cycloalkyl, —OH, —OC$_{3-10}$ cycloalkyl, —OC$_{1-10}$ alkyl or $C_{1-10}$ alkyl.

Generally R$^{10}$ is H, $C_{3-10}$ cycloalkyl or $C_{1-10}$ alkyl. Usually R$^{10}$ is $C_{1-10}$ alkyl or $C_{3-10}$ cycloalkyl. Preferred R$^{10}$ is isopropyl, isobutyl, cyclohexyl or cyclopropyl.

Generally R$^{11}$ is H or $C_{1-10}$ alkyl.

Generally R$^{12}$ is H or $C_{1-10}$ alkyl.

Generally R$^{13}$ is H, $C_{3-10}$ cycloalkyl, —OH, —OC$_{3-10}$ cycloalkyl, —OC$_{1-10}$ alkyl or $C_{1-10}$ alkyl.

Generally R$^{14}$ is H, $C_{3-10}$ cycloalkyl or $C_{1-10}$ alkyl.

Generally R$^{15}$ is H or $C_{1-10}$ alkyl.

Generally R$^{16}$ is H or $C_{1-10}$ alkyl.

Generally R$^{17}$ is H, $C_{3-10}$ cycloalkyl, —OH, —OC$_{3-10}$ cycloalkyl, —OC$_{1-10}$ alkyl or $C_{1-10}$ alkyl.

Generally R$^{18}$ is H, $C_{3-10}$ cycloalkyl or $C_{1-10}$ alkyl.

Generally R$^{19}$ is H or $C_{1-10}$ alkyl.

Generally R$^{20}$ is H or $C_{1-10}$ alkyl.

Generally R$^{21}$ is H, $C_{3-10}$ cycloalkyl, —OH, —OC$_{3-10}$ cycloalkyl, —OC$_{1-10}$ alkyl or $C_{1-10}$ alkyl.

Generally R$^{22}$ is H, $C_{3-10}$ cycloalkyl or $C_{1-10}$ alkyl.

Generally R$^{23}$ is H or $C_{1-10}$ alkyl.

Generally R$^{24}$ is H or $C_{1-10}$ alkyl.

Generally R$^{25}$ is H, $C_{3-10}$ cycloalkyl, —OH, —OC$_{3-10}$ cycloalkyl, —OC$_{1-10}$ alkyl or $C_{1-10}$ alkyl.

Generally a is 0, 1, 2 or 3. Usually a is 0.

Generally b is 0, 1, 2 or 3. Usually b is 0.

Generally c is 0, 1, 2 or 3. Usually c is 0.

In a preferred embodiment of the invention

R is H, nitrile, $C_{1-10}$ alkyl, halogen or nitrogen dioxide; and

R$^1$ is $C_{1-10}$ alkyl, OR$^{10}$, or heterocycle; and

R$^2$ is H, halogen or $C_{1-10}$ alkyl; and a is 0; and b is 0; and c is 0; and R$^{10}$ is isopropyl, isobutyl, cyclohexyl or cyclopropyl.

In a more preferred embodiment of the invention

R is H, nitrile, bromine, trifluoromethyl, nitrogen dioxide, methyl or chlorine; and R$^1$ is isopropoxy, cyclopropoxy, isobutoxy or 2-methylpiperdin-1-yl; and R$^2$ is H, methyl, trifluoromethyl or chlorine; and a is 0; and b is 0; and c is 0; and R$^{10}$ is isopropyl or cyclopropyl.

Compounds of the invention are:

3-(4-Imidazol-1-ylmethyl-phenyl)-5-(4-isobutyl-phenyl)-[1,2,4]oxadiazole;

5-[3-(4-Imidazol-1-ylmethyl-phenyl)-[1,2,4]oxadiazol-5-yl]-2-isopropoxy-benzonitrile;

3-(4-Imidazol-1-ylmethyl-phenyl)-5-(4-isobutoxy-3-trifluoromethyl-phenyl)-[1,2,4]oxadiazole;

5-(4-Cyclohexyloxy-3-trifluoromethyl-phenyl)-3-(4-imidazol-1-ylmethyl-phenyl)-[1,2,4]oxadiazole;

3-(4-Imidazol-1-ylmethyl-phenyl)-5-(4-isopropoxy-3-trifluoromethyl-phenyl)-[1,2,4]oxadiazole;

5-(3-Chloro-4-isopropoxy-phenyl)-3-(4-imidazol-1-ylmethyl-phenyl)-[1,2,4]oxadiazole;

5-(3-Bromo-4-isopropoxy-phenyl)-3-(4-imidazol-1-ylmethyl-phenyl)-[1,2,4]oxadiazole;

5-[3-(4-Imidazol-1-ylmethyl-phenyl)-[1,2,4]oxadiazol-5-yl]-2-isobutoxy-benzonitrile;

3-(4-Imidazol-1-ylmethyl-phenyl)-5-(4-isopropoxy-phenyl)-[1,2,4]oxadiazole;

3-(4-Imidazol-1-ylmethyl-phenyl)-5-(4-isopropoxy-3-methyl-phenyl)-[1,2,4]oxadiazole;

3-(4-Imidazol-1-ylmethyl-phenyl)-5-(4-isopropoxy-3-nitro-phenyl)-[1,2,4]oxadiazole;

5-(3-Bromo-4-isobutoxy-phenyl)-3-(4-imidazol-1-ylmethyl-phenyl)-[1,2,4]oxadiazole;

5-[3-(4-Imidazol-1-ylmethyl-2-methyl-phenyl)-[1,2,4]oxadiazol-5-yl]-2-isopropoxy-benzonitrile;

3-(4-Imidazol-1-ylmethyl-2-methyl-phenyl)-5-(4-isopropoxy-3-nitro-phenyl)-[1,2,4]oxadiazole;

5-(3-Bromo-4-isopropoxy-phenyl)-3-(4-imidazol-1-ylmethyl-2-methyl-phenyl)-[1,2,4]oxadiazole;

5-(3-Bromo-4-cyclopropoxy-phenyl)-3-(4-imidazol-1-ylmethyl-phenyl)-[1,2,4]oxadiazole;

5-(3-Bromo-4-cyclopropoxy-phenyl)-3-(4-imidazol-1-ylmethyl-2-methyl-phenyl)-[1,2,4]oxadiazole;

3-(4-Imidazol-1-ylmethyl-2-methyl-phenyl)-5-(4-isopropoxy-3-trifluoromethyl-phenyl)-[1,2,4]oxadiazole;

3-(4-Imidazol-1-ylmethyl-2-methyl-phenyl)-5-(4-isopropoxy-3-methyl-phenyl)-[1,2,4]oxadiazole;

5-[3-(4-Imidazol-1-ylmethyl-2-trifluoromethyl-phenyl)-[1,2,4]oxadiazol-5-yl]-2-isopropoxy-benzonitrile;
5-(3-Bromo-4-isopropoxy-phenyl)-3-(4-imidazol-1-ylmethyl-2-trifluoromethyl-phenyl)-[1,2,4]oxadiazole;
3-[4-(1H-imidazol-1-ylmethyl)-2-(trifluoromethyl)phenyl]-5-(4-isopropoxy-3-methylphenyl)-1,2,4-oxadiazole;
3-[4-(1H-imidazol-1-ylmethyl)-2-(trifluoromethyl)phenyl]-5-[4-isopropoxy-3-(trifluoromethyl)phenyl]-1,2,4-oxadiazole;
3-[4-(1H-imidazol-1-ylmethyl)-2-(trifluoromethyl)phenyl]-5-(4-isopropoxy-3-nitrophenyl)-1,2,4-oxadiazole;
5-[3-bromo-4-(cyclopropyloxy)phenyl]-3-[4-(1H-imidazol-1-ylmethyl)-2-(trifluoromethyl)phenyl]-1,2,4-oxadiazole;
5-(3-bromo-4-isobutoxyphenyl)-3-[4-(1H-imidazol-1-ylmethyl)-2-(trifluoromethyl)phenyl]-1,2,4-oxadiazole;
5-{3-[2-chloro-4-(1H-imidazol-1-ylmethyl)phenyl]-1,2,4-oxadiazol-5-yl}-2-isopropoxybenzonitrile;
5-(3-bromo-4-isopropoxyphenyl)-3-[2-chloro-4-(1H-imidazol-1-ylmethyl)phenyl]-1,2,4-oxadiazole;
3-[2-chloro-4-(1H-imidazol-1-ylmethyl)phenyl]-5-[4-isopropoxy-3-(trifluoromethyl)phenyl]-1,2,4-oxadiazole;
3-[2-chloro-4-(1H-imidazol-1-ylmethyl)phenyl]-5-(4-isopropoxy-3-nitrophenyl)-1,2,4-oxadiazole;
5-{3-[4-(1H-imidazol-1-ylmethyl)phenyl]-1,2,4-oxadiazol-5-yl}-2-(2-methylpiperidin-1-yl)benzonitrile.

Preferred compounds of the invention are:
5-[3-(4-Imidazol-1-ylmethyl-phenyl)[1,2,4]oxadiazol-5-yl]-2-isopropoxy-benzonitrile;
5-(3-Chloro-4-isopropoxy-phenyl)-3-(4-imidazol-1-ylmethyl-phenyl)-[1,2,4]oxadiazole;
5-(3-Bromo-4-isopropoxy-phenyl)-3-(4-imidazol-1-ylmethyl-phenyl)-[1,2,4]oxadiazole;
3-(4-Imidazol-1-ylmethyl-phenyl)-5-(4-isopropoxy-3-methyl-phenyl)-[1,2,4]oxadiazole;
3-(4-Imidazol-1-ylmethyl-phenyl)-5-(4-isopropoxy-3-nitro-phenyl)-[1,2,4]oxadiazole;
5-[3-(4-Imidazol-1-ylmethyl-2-methyl-phenyl)-[1,2,4]oxadiazol-5-yl]-2-isopropoxy-benzonitrile;
3-(4-Imidazol-1-ylmethyl-2-methyl-phenyl)-5-(4-isopropoxy-3-nitro-phenyl)-[1,2,4]oxadiazole;
5-(3-Bromo-4-isopropoxy-phenyl)-3-(4-imidazol-1-ylmethyl-2-methyl-phenyl)-[1,2,4]oxadiazole;
5-(3-Bromo-4-cyclopropoxy-phenyl)-3-(4-imidazol-1-ylmethyl-phenyl)-[1,2,4]oxadiazole;
5-(3-Bromo-4-cyclopropoxy-phenyl)-3-(4-imidazol-1-ylmethyl-2-methyl-phenyl)-[1,2,4]oxadiazole;
3-(4-Imidazol-1-ylmethyl-2-methyl-phenyl)-5-(4-isopropoxy-3-trifluoromethyl-phenyl)-[1,2,4]oxadiazole;
3-(4-Imidazol-1-ylmethyl-2-methyl-phenyl)-5-(4-isopropoxy-3-methyl-phenyl)-[1,2,4]oxadiazole;
5-[3-(4-Imidazol-1-ylmethyl-2-trifluoromethyl-phenyl)-[1,2,4]oxadiazol-5-yl]-2-isopropoxy-benzonitrile;
3-[4-(1H-imidazol-1-ylmethyl)-2-(trifluoromethyl)phenyl]-5-(4-isopropoxy-3-nitrophenyl)-1,2,4-oxadiazole;
5-{3-[2-chloro-4-(1H-imidazol-1-ylmethyl)phenyl]-1,2,4-oxadiazol-5-yl}-2-isopropoxybenzonitrile;
5-(3-bromo-4-isopropoxyphenyl)-3-[2-chloro-4-(1H-imidazol-1-ylmethyl)phenyl]-1,2,4-oxadiazole;
3-[2-chloro-4-(1H-imidazol-1-ylmethyl)phenyl]-5-[4-isopropoxy-3-(trifluoromethyl)phenyl]-1,2,4-oxadiazole;
3-[2-chloro-4-(1H-imidazol-1-ylmethyl)phenyl]-5-(4-isopropoxy-3-nitrophenyl)-1,2,4-oxadiazole.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic, for example, a hydrohalic such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zurich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4)

lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I.

The compounds of formula I according to the invention can be prepared analogously to conventional methods as understood by the person skilled in the art of synthetic organic chemistry.

The synthetic scheme set forth below, illustrates how compounds according to the invention can be made. Those skilled in the art will be able to routinely modify and/or adapt the following scheme to synthesize any compounds of the invention covered by Formula I.

Formula I

To a solution of benzoic acid (a) (1 mmol) in THF (8 mL) was added 1,1'-carbonyldiimidazole (CDI) (1.1 mmol). The mixture was stirred at room temperature for 30 minutes. To the reaction mixture was added imidazole derivative (b) (1.1 mmol) and N,N-dimethylformamide (DMF) (8 mL); the resulting mixture was stirred at 50° C. for 2 hours. The reaction mixture was then transferred to a microwave (MWI) vial and heated at 150° C. for 20 minutes. After cooling to room temperature the mixture was diluted with water and extracted with ethyl acetate. The ethyl acetate phase was washed with water and brine, dried over sodium sulfate and concentrated. Trituration or column chromatography (methanol/ethyl acetate) gave the corresponding compound of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

The IUPAC names of the compounds mentioned in the examples were generated with ACD version 8.

Unless specified otherwise in the examples, characterization of the compounds is performed according to the following methods:

NMR spectra are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluka, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported.

The following abbreviations are used in the examples:

| | |
|---|---|
| DMF | N,N-dimethylformamide |
| NaOH | sodium hydroxide |
| CD$_3$OD | deuterated methanol |
| HCl | hydrochloric acid |
| CDCl$_3$ | deuterated chloroform |
| DMSO-d$_6$ | deuterated dimethyl sulfoxide |
| CU | 1,1'-carbonyldiimidazole |
| Et$_2$Zn | diethylzinc |
| NH$_4$Cl | ammonium chloride |
| CH$_2$Cl$_2$ | dichloromethane |
| K$_2$CO$_3$ | potassium carbonate |
| MPLC | medium pressure liquid chromatography |
| THF | tetrahydrofuran |
| [IrCl(cod)]$_2$ | di-μ-chlorobis(1,5-cyclooctadiene)diiridium(I) |
| ClCH$_2$I | chloroiodomethane |

Those skilled in the art will be able to routinely modify and/or adapt the following schemes to synthesize any compound of the invention covered by Formula I.

Some compounds of this invention can generally be prepared in one step from commercially available literature starting materials.

Example 1

Intermediate 1

4-((1H-Imidazol-1-yl)methyl)-2-methylbenzonitrile

To the suspension of potassium carbonate (2.16 g, 15.7 mmol) in THF at room temperature was added imidazole (4.27 g, 62.8 mmol). The mixture was stirred at room temperature for 10 minutes then 4-(bromomethyl)-2-methylbenzonitrile (CAS 1001055-64-6) (6.6 g, 31.4 mmol) was added and refluxed for 24 hours. The mixture was then cooled to room temperature. Potassium carbonate was filtered off. The filtrate was concentrated and residue was redissolved in dichloromethane. The dichloromethane phase was washed with water (three times) and then HCl (three times). To the combined HCl phase was added sodium carbonate (solid) and extracted with ethyl acetate. Ethyl acetate phase was washed with water and brine, dried over sodium sulfate and concentrated. Column chromatography (10% methanol/ethyl acetate) gave 4-((1H-imidazol-1-yl)methyl)-2-methylbenzonitrile (3.59 g, 58%) as a white solid.

$^1$H NMR (300 MHz, CDCl$_3$) δ 2.42 (s, 3H), 5.10 (s, 2H), 6.84 (s, 1H), 6.95-7.02 (m, 3H), 7.48 (m, 2H).

Example 2

Intermediate 2

Ethyl 3-bromo-4-(vinyloxy)benzoate

To a toluene (8 mL) solution of [IrCl(cod)]$_2$ (54 mg, 0.08 mmol) and sodium carbonate (506 mg, 4.8 mmol) was added ethyl 3-bromo-4-hydroxybenzoate (CAS 37470-58-9) (1.95 g, 7.96 mmol) followed by vinyl acetate (1.5 mL, 15.9 mmol) under argon. The mixture was stirred at 100° C. for 2 hours. The mixture was cooled to room temperature, quenched with wet ether. Solid was filtered off and washed with ether. Column chromatography (3% ethyl acetate/hexane) gave ethyl 3-bromo-4-(vinyloxy)benzoate (1.77 g, 79%) as a yellow oil.

$^1$H NMR (300 MHz, CDCl$_3$) δ 1.39 (t, J=7.2 Hz, 3H), 4.37 (t, J=7.2 Hz, 2H), 4.65-4.67 (m, 1H), 4.92-4.97 (m, 1H), 6.59-6.66 (m, 1H), 7.02-7.05 (m, 1H), 7.96-7.99 (m, 1H), 8.27 (s, 1H).

Example 3

Intermediate 3

Ethyl 3-bromo-4-cyclopropoxybenzoate

To a solution of Intermediate 2 (500 mg, 1.76 mmol), ClCH$_2$I (0.41 mL, 5.66 mmol) in dichloroethane (6 mL) at −5° C. was added Et$_2$Zn (2.3 mL, 1.2M in CH$_2$Cl$_2$, 2.82 mmol). The mixture was stirred at room temperature for 1 hour. The reaction was quenched with NH$_4$Cl(sat.) and extracted with ether. Ether phase was washed with water and brine, dried over sodium sulfate and concentrated to give ethyl 3-bromo-4-cyclopropoxybenzoate (500 mg, 100%) as a yellow solid.

$^1$H NMR (300 MHz, CDCl$_3$) δ 0.88 (m, 4H), 1.38 (t, J=7.2 Hz, 3H), 3.85-3.89 (m, 1H), 4.36 (t, J=7.2 Hz, 2H), 7.27-7.30 (m, 1H), 7.97-8.00 (m, 1H), 8.21 (s, 1H).

Example 4

Intermediate 4

3-Bromo-4-cyclopropoxybenzoic acid

To a solution of Intermediate 3 (2.2 g, 7.7 mmol) in methanol (20 mL) was added NaOH (2M, 20 mL). The mixture was refluxed for 16 hours. The mixture was cooled room temperature, diluted with water and extracted with ethyl acetate/hexane (1:5). The aqueous phase was added HCl and extracted with ethyl acetate.

Ethyl acetate phase was washed with water and brine, dried over sodium sulfate and concentrated to give 3-bromo-4-cyclopropoxybenzoic acid (1.8 g, 90%) as a white solid.

$^1$H NMR (300 MHz, CDCl$_3$) δ 0.90 (m, 4H), 3.87-3.90 (m, 1H), 7.31-7.34 (m, 1H), 8.03-8.07 (m, 1H), 8.28 (s, 1H).

Example 5

Compound 1

5-(3-Bromo-4-cyclopropoxy-phenyl)-3-(4-imidazol-1-ylmethyl-phenyl)-[1,2,4]oxadiazole To a solution of Intermediate 4 benzoic acid (1 mmol) in THF (8 mL) was added CU (1.1 mmol). The mixture was stirred at room temperature for 30 minutes. To the reaction mixture was added benzonitrile-4-(1H-imidazol-1-ylmethyl) CAS 112809-54-8 (1.1 mmol) and DMF (8 mL) and resulting mixture was stirred at 50° C. for 2 hours. The reaction mixture was then transferred to a microwave vial and heated at 150° C. for 20 minutes. After cooling to room temperature the mixture was diluted with water and extracted with ethyl acetate. Ethyl acetate phase was washed with water and brine, dried over sodium sulfate and concentrated. Trituration or column chromatography (methanol/ethyl acetate) gave 5-(3-Bromo-4-cyclopropoxy-phenyl)-3-(4-imidazol-1-ylmethyl-phenyl)-[1,2,4]oxadiazole.

$^1$H NMR (300 MHz, CDCl$_3$) 0.91-0.93 (m, 4H), 3.89-3.91 (m, 1H), 5.21 (s, 2H), 6.94 (s, 1H), 7.14 (s, 1H), 7.27-7.30 (m, 2H), 7.40-7.43 (m, 1H), 7.62 (s, 1H), 8.12-8.16 (m, 3H), 8.39 (s, 1H).

Compounds 2-6 were prepared from the corresponding benzoic acids and the corresponding imidazole derivatives, in a similar manner to the method described in Example 5 for Compound 1. The reactants used and the results are described below in Table 1.

TABLE 1

| Compound number | IUPAC name | Reactant(s) | $^1$H NMR δ (ppm) for Compound |
|---|---|---|---|
| 2 | 5-(3-Bromo-4-cyclopropoxy-phenyl)-3-(4-imidazol-1-ylmethyl-2-methyl-phenyl)-[1,2,4]oxadiazole | Intermediate 1 Intermediate 4 | $^1$H NMR (300 MHz, CDCl$_3$) δ 0.91-0.93(m, 4H), 2.65(s, 3H), 3.90(m, 1H), 5.17(s, 2H), 6.94(s, 1H), 7.11-7.13(m, 3H), 7.40-7.43(m, 1H), 7.62(s, 1H), 8.06-8.14(m, 2H), 8.39(s, 1H) |
| 3 | 3-(4-Imidazol-1-ylmethyl-phenyl)-5-(4-isopropoxy-3-trifluoromethyl-phenyl)-[1,2,4]oxadiazole | Benzonitrile, 4-(1H-imidazol-1-ylmethyl)-[CAS 112809-54-8] Benzoic acid, 4-(1-methylethoxy)-3-(trifluoromethyl)-[CAS 213598-16-4] | $^1$H NMR (300 MHz, CD$_3$OD) δ 1.42-1.44(m, 6H), 4.76-4.80(m, 1H), 5.21(s, 2H), 6.94(s, 1H), 7.13-7.15(m, 2H), 7.26-7.29(m, 2H), 7.61(s, 1H), 8.13-8.16(m, 2H), 8.27-8.30(m, 1H), 8.41(s, 1H) |
| 4 | 3-(4-Imidazol-1-ylmethyl-phenyl)-5-(4-isobutoxy-3-trifluoromethyl-phenyl)-[1,2,4]oxadiazole | Benzonitrile, 4-(1H-imidazol-1-ylmethyl)-[CAS 112809-54-8] Benzoic acid, 4-(2-methylpropoxy)-3-(trifluoromethyl)-[CAS 1008769-62-7] | $^1$H NMR (300 MHz, CD$_3$OD) δ 1.07-1.09(m, 6H), 2.10-2.17(m, 1H), 3.98-4.00(m, 2H), 5.33(s, 2H), 7.03(s, 1H), 7.17(s, 1H), 7.36-7.42(m, 3H), 7.81(s, 1H), 8.11-8.14(m, 2H), 8.36-8.38(m, 2H) |
| 5 | 5-(4-Cyclohexyloxy-3-trifluoromethyl-phenyl)-3-(4-imidazol-1-ylmethyl-phenyl)-[1,2,4]oxadiazole | Benzonitrile, 4-(1H-imidazol-1-ylmethyl)-[CAS 112809-54-8] Benzoic acid, 4-(cyclohexyloxy)-3-(trifluoromethyl)-[CAS 1008769-64-9] | $^1$H NMR (300 MHz, CD$_3$OD) δ 1.4-1.6(m, 4H), 1.6-2.0(m, 6H), 4.5-4.6(m, 1H), 5.21(s, 2H), 6.94(s, 1H), 7.14(br, 2H), 7.27-7.29(m, 2H), 7.61(s, 1H), 8.14-8.16(m, 2H), 8.26-8.29(m, 1H), 8.42(s, 1H) |
| 6 | 3-(4-Imidazol-1-ylmethyl-2-methyl-phenyl)-5-(4-isopropoxy-3-trifluoromethyl-phenyl)-[1,2,4]oxadiazole | Intermediate 1 Benzoic acid, 4-(1-methylethoxy)-3-(trifluoromethyl)-[CAS 213598-16-4] | $^1$H NMR (300 MHz, CDCl$_3$) δ 1.43-1.45(m, 6H), 2.66(s, 3H), 4.74-4.82(m, 1H), 5.17(s, 2H), 6.94(s, 1H), 7.12-7.16(m, 4H), 7.65(s, 1H), 8.06-8.09(m, 1H), 8.29-8.32(m, 1H), 8.42(s, 1H) |

Example 6

Compound 7

3-(4-Imidazol-1-ylmethyl-phenyl)-5-(4-isopropoxy-3-nitro-phenyl)-[1,2,4]oxadiazole The suspension of 4-isopropoxy-3-nitrobenzoic acid CAS 156629-52-6 (1.27 mmol), 4-Benzonitrile, (1H-imidazol-1-ylmethyl) CAS 112809-54-8 (1.41 mmol) and $K_2CO_3$ (1.41 mmol) in toluene (2 mL) and DMF (2 mL) in microwave vial was heated at 180° C. for 2-5 hours. The mixture was cooled to room temperature and diluted with water, extracted with dichloromethane. The dichloromethane phase was washed with water and brine, dried over sodium sulfate and concentrated. MPLC (50% MeOH/$CH_2Cl_2$) followed by recrystalization (ethylacetate/hexane) gave 3-(4-Imidazol-1-ylmethyl-phenyl)-5-(4-isopropoxy-3-nitro-phenyl)-[1,2,4] oxadiazole (60 mg, 12%) as a white solid.

$^1$H NMR (300 MHz, $CD_3OD$) δ 1.41-1.43 (d, J=5.86, 6H), 4.85-4.97 (m, 1H), 5.33 (s, 2H), 7.03 (s, 1H), 7.17 (s, 1H), 7.39-7.42 (m, 2H), 7.50-7.53 (m, 1H), 7.81 (s, 1H), 8.11-8.14 (m, 2H), 8.34-8.37 (m, 1H), 8.55 (s, 1H).

Compounds 8-17 were prepared from the corresponding benzoic acids and the corresponding imidazole derivatives, in a similar manner to the method described in Example 6 for Compound 7. The reactants used and the results are described below in Table 2.

TABLE 2

| Compound number | IUPAC name | Reactant(s) used | $^1$H NMR δ (ppm) for Compound |
|---|---|---|---|
| 8 | 5-[3-(4-Imidazol-1-ylmethyl-phenyl)-[1,2,4]oxadiazol-5-yl]-2-isobutoxy-benzonitrile | Benzonitrile, 4-(1H-imidazol-1-ylmethyl)-[CAS 112809-54-8] Benzoic acid, 3-cyano-4-(2-methylpropoxy)-[CAS 528607-60-5] | $^1$H NMR (300 MHz, $CD_3OD$) δ 1.10-1.12(d, J = 6.74, 6H), 2.16-2.21(m, 1H), 4.03-4.05(m, 2H), 5.33(s, 2H), 7.03(s, 1H), 7.17(s, 1H), 7.38-7.42(m, 3H), 7.80(s, 1H), 8.11-8.14(m, 2H), 8.39-8.44(m, 2H) |
| 9 | 5-(3-Bromo-4-isobutoxy-phenyl)-3-(4-imidazol-1-ylmethyl-phenyl)-[1,2,4]oxadiazole | Benzonitrile, 4-(1H-imidazol-1-ylmethyl)-[CAS 112809-54-8] Benzoic acid, 3-bromo-4-(2-methylpropoxy)-[CAS 881583-05-7] | $^1$H NMR (300 MHz, $CDCl_3$) δ 1.09-1.11(d, J = 6.74, 6H), 2.18-2.23(m, 1H), 3.87-3.89(m, 2H), 5.20(s, 2H), 6.94-7.00(m, 2H), 7.13(s, 1H), 7.26-7.28(m, 2H), 7.60(s, 1H), 8.07-8.15(m, 3H), 8.39(s, 1H) |
| 10 | 3-(4-Imidazol-1-ylmethyl-phenyl)-5-(4-isobutyl-phenyl)-[1,2,4]oxadiazole | Benzonitrile, 4-(1H-imidazol-1-ylmethyl)-[CAS 112809-54-8] Benzoic acid, 4-(2-methylpropyl)-[CAS 38861-88-0] | $^1$H NMR (300 MHz, $CD_3OD$) δ 0.89-0.91 (d, J = 6.45, 6H), 1.86-1.91(m, 1H), 2.52-2.54(m, 2H), 5.28(s, 2H), 7.02(s, 1H), 7.13(s, 1H), 7.31-7.36(m, 4H), 7.79(s, 1H), 8.01-8.08(m, 4H) |
| 11 | 3-(4-Imidazol-1-ylmethyl-phenyl)-5-(4-isopropoxy-phenyl)-[1,2,4]oxadiazole | Benzonitrile, 4-(1H-imidazol-1-ylmethyl)-[CAS 112809-54-8] Benzoic acid, 4-(1-methylethoxy)-[CAS 13205-46-4] | $^1$H NMR (300 MHz, $CDCl_3$) δ 1.39-1.41(d, J = 5.86, 6H), 4.64-4.72(m, 1H), 5.21(s, 2H), 6.94(s, 1H), 7.00-7.02(m, 2H), 7.13(s, 1H), 7.26-7.29(m, 2H), 7.61(s, 1H), 8.12-8.17(m, 4H) |
| 12 | 5-[3-(4-Imidazol-1-ylmethyl-phenyl)-[1,2,4]oxadiazol-5-yl]-2-isopropoxy-benzonitrile | Benzonitrile, 4-(1H-imidazol-1-ylmethyl)-[CAS 112809-54-8] Benzoic acid, 3-cyano-4-(1-methylethoxy)-[CAS 258273-31-3] | $^1$H NMR (300 MHz, DMSO) δ 1.36-1.38(d, J = 5.86, 6H), 4.94-4.98(m, 1H), 5.31(s, 2H), 6.93(s, 1H), 7.22(s, 1H), 7.41-7.44(m, 2H), 7.52-7.55(m, 1H), 7.78(s, 1H), 8.04-8.07(m, 2H), 8.36-8.39(m, 1H), 8.47(s, 1H) |
| 13 | 5-[3-(4-Imidazol-1-ylmethyl-2-methyl-phenyl)-[1,2,4]oxadiazol-5-yl]-2-isopropoxy-benzonitrile | Intremediate 1 Benzoic acid, 3-cyano-4-(1-methylethoxy)-[CAS 258273-31-3] | $^1$H NMR (300 MHz, $CDCl_3$) δ 1.47-1.49(d, J = 5.86, 6H), 2.65(s, 3H), 4.73-4.80(m, 1H), 5.17(s, 2H), 6.94(s, 1H), 7.11-7.13(m, 4H), 7.61(s, 1H), 8.06-8.08(m, 1H), 8.31-8.34(m, 1H), 8.41(s, 1H) |
| 14 | 5-(3-Bromo-4-isopropoxy-phenyl)-3-(4-imidazol-1-ylmethyl-phenyl)-[1,2,4]oxadiazole | Benzonitrile, 4-(1H-imidazol-1-ylmethyl)-[CAS 112809-54-8] Benzoic acid, 3-bromo-4-(1-methylethoxy)-[CAS 213598-20-0] | $^1$H NMR (300 MHz, $CDCl_3$) δ 1.44-1.46(d, J = 5.86, 6H), 4.69-4.73(m, 1H), 5.21(s, 2H), 6.95(s, 1H), 7.00-7.03(m, 1H), 7.14(s, 1H), 7.27-7.30(m, 2H), 7.65(s, 1H), 8.08-8.16(m, 3H), 8.41(s, 1H) |
| 15 | 5-(3-Bromo-4-isopropoxy-phenyl)-3-(4-imidazol-1-ylmethyl-2-methyl-phenyl)- | Intremediate 1 Benzoic acid, 3-bromo-4-(1-methylethoxy)-[CAS 213598-20-0] | $^1$H NMR (300 MHz, $CDCl_3$) δ 1.44-1.46(d, J = 5.86, 6H), 2.65(s, 3H), 4.67-4.75(m, 1H), 5.17(s, 2H), 6.94(s, 1H), 7.00-7.03(m, 1H), |

TABLE 2-continued

| Compound number | IUPAC name | Reactant(s) used | $^1$H NMR δ (ppm) for Compound |
|---|---|---|---|
| | [1,2,4]oxadiazole | | 7.11-7.14(m, 3H), 7.64(s, 1H), 8.05-8.11(m, 2H), 8.41(s, 1H) |
| 16 | 5-(3-Chloro-4-isopropoxy-phenyl)-3-(4-imidazol-1-ylmethyl-phenyl)-[1,2,4]oxadiazole | Benzonitrile, 4-(1H-imidazol-1-ylmethyl)- [CAS 112809-54-8] Benzoic acid, 3-chloro-4-(1-methylethoxy)- [CAS 213598-07-3] | $^1$H NMR (300 MHz, CDCl$_3$) δ 1.44-1.46(d, J = 5.86, 6H), 4.70-4.73(m, 1H), 5.21(s, 2H), 6.94(s, 1H), 7.04-7.07(m, 1H), 7.14(s, 1H), 7.27-7.30(m, 2H), 7.64(s, 1H), 8.04-8.07(m, 1H), 8.14-8.16(m, 2H), 8.23(s, 1H) |
| 17 | 3-(4-Imidazol-1-ylmethyl-phenyl)-5-(4-isopropoxy-3-methyl-phenyl)-[1,2,4]oxadiazole | Benzonitrile, 4-(1H-imidazol-1-ylmethyl)- [CAS 112809-54-8] Benzoic acid, 3-methyl-4-(1-methylethoxy [CAS 856165-81-6] | $^1$H NMR (300 MHz, CD$_3$OD) δ 1.37-1.39(d, J = 6.15, 6H), 2.25(s, 3H), 4.73-4.77(m, 1H), 5.32(s, 2H), 7.02(s, 1H), 7.07-7.10(m, 1H), 7.16(s, 1H), 7.38-7.41(m, 2H), 7.80(s, 1H), 7.95-8.00(m, 2H), 8.09-8.12(m, 2H) |
| 18 | 3-(4-Imidazol-1-ylmethyl-2-methyl-phenyl)-5-(4-isopropoxy-3-methyl-phenyl)-[1,2,4]oxadiazole | Intermediate 1 Benzoic acid, 3-methyl-4-(1-methylethoxy [CAS 856165-81-6] | $^1$H NMR (300 MHz, CDCl$_3$) δ 1.40(d, J = 5.86, 6H), 2.28(s, 3H), 2.65(s, 3H), 4.65-4.69(m, 1H), 5.17(s, 2H), 6.93-6.95(m, 2H), 7.10-7.13(m, 3H), 7.63(s, 1H), 8.01-8.08(m, 3H) |
| 19 | 3-(4-Imidazol-1-ylmethyl-2-methyl-phenyl)-5-(4-isopropoxy-3-nitro-phenyl)-[1,2,4]oxadiazole | Intermediate 1 Benzoic acid, 4-(1-methylethoxy)-3-nitro- [CAS 156629-52-6] | $^1$H NMR (300 MHz, CDCl$_3$) δ 1.46-1.48(d, J = 5.86, 6H), 2.66(s, 3H), 4.79-4.85(m, 1H), 5.18(s, 2H), 6.94(s, 1H), 7.12-7.14(m, 3H), 7.22-7.25(m, 1H), 7.63(s, 1H), 8.06-8.09(m, 1H), 8.29-8.33(m, 1H), 8.62-8.64(m, 1H) |

Biological Data:

Novel compounds were synthesized and tested for S1P1 activity using the GTP γ$^{35}$S binding assay. These compounds may be assessed for their ability to activate or block activation of the human S1P1 receptor in cells stably expressing the S1P1 receptor. GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

| Biological Data: Intrinsic Activity | S1P1 GTPγ$^{35}$S EC50 (nM) | % S1P1 STIMU-LATION @ 5 μM (%) |
|---|---|---|
| 3-(4-Imidazol-1-ylmethyl-phenyl)-5-(4-isobutyl-phenyl)-[1,2,4]oxadiazole | 543 | 79.8 |
| 5-[3-(4-Imidazol-1-ylmethyl-phenyl)-[1,2,4]oxadiazol-5-yl]-2-isopropoxy-benzonitrile | 3.31 | 94.6 |
| 3-(4-Imidazol-1-ylmethyl-phenyl)-5-(4-isobutoxy-3-trifluoromethyl-phenyl)-[1,2,4]oxadiazole | 998 | 72.2 |
| 5-(4-Cyclohexyloxy-3-trifluoromethyl-phenyl)-3-(4-imidazol-1-ylmethyl-phenyl)-[1,2,4]oxadiazole | 149 | 91.8 |
| 3-(4-Imidazol-1-ylmethyl-phenyl)-5-(4-isopropoxy-3-trifluoromethyl-phenyl)-[1,2,4]oxadiazole | 0.51 | 95.6 |
| 5-(3-Chloro-4-isopropoxy-phenyl)-3-(4-imidazol-1-ylmethyl-phenyl)-[1,2,4]oxadiazole | 2.79 | 99.8 |
| 5-(3-Bromo-4-isopropoxy-phenyl)-3-(4-imidazol-1-ylmethyl-phenyl)-[1,2,4]oxadiazole | 0.92 | 93.9 |
| 5-[3-(4-Imidazol-1-ylmethyl-phenyl)-[1,2,4]oxadiazol-5-yl]-2-isobutoxy-benzonitrile | 62 | 75.9 |
| 3-(4-Imidazol-1-ylmethyl-phenyl)-5-(4-isopropoxy-phenyl)-[1,2,4]oxadiazole | 453 | 92.8 |
| 3-(4-Imidazol-1-ylmethyl-phenyl)-5-(4-isopropoxy-3-methyl-phenyl)-[1,2,4]oxadiazole | 10.3 | 133 |
| 3-(4-Imidazol-1-ylmethyl-phenyl)-5-(4-isopropoxy-3-nitro-phenyl)-[1,2,4]oxadiazole | 3.24 | 118 |
| 5-(3-Bromo-4-isobutoxy-phenyl)-3-(4-imidazol-1-ylmethyl-phenyl)-[1,2,4]oxadiazole | 28.6 | 86.2 |

| Biological Data: Intrinsic Activity | S1P1 GTPγ35S EC50 (nM) | % S1P1 STIMULATION @ 5 µM (%) |
|---|---|---|
| 5-[3-(4-Imidazol-1-ylmethyl-2-methyl-phenyl)-[1,2,4]oxadiazol-5-yl]-2-isopropoxy-benzonitrile | 4.76 | 96.4 |
| 3-(4-Imidazol-1-ylmethyl-2-methyl-phenyl)-5-(4-isopropoxy-3-nitro-phenyl)-[1,2,4]oxadiazole | 8.98 | 102 |
| 5-(3-Bromo-4-isopropoxy-phenyl)-3-(4-imidazol-1-ylmethyl-2-methyl-phenyl)-[1,2,4]oxadiazole | 19.6 | 109 |
| 5-(3-Bromo-4-cyclopropoxy-phenyl)-3-(4-imidazol-1-ylmethyl-phenyl)-[1,2,4]oxadiazole | 14.4 | 99.9 |
| 5-(3-Bromo-4-cyclopropoxy-phenyl)-3-(4-imidazol-1-ylmethyl-2-methyl-phenyl)-[1,2,4]oxadiazole | 32 | 96 |
| 3-(4-Imidazol-1-ylmethyl-2-methyl-phenyl)-5-(4-isopropoxy-3-trifluoromethyl-phenyl)-[1,2,4]oxadiazole | 3.38 | 95.5 |
| 3-(4-Imidazol-1-ylmethyl-2-methyl-phenyl)-5-(4-isopropoxy-3-methyl-phenyl)-[1,2,4]oxadiazole | 19.8 | 94.6 |
| 5-[3-(4-Imidazol-1-ylmethyl-2-trifluoromethyl-phenyl)-[1,2,4]oxadiazol-5-yl]-2-isopropoxy-benzonitrile | 5.22 | 97.6 |
| 5-(3-Bromo-4-isopropoxy-phenyl)-3-(4-imidazol-1-ylmethyl-2-trifluoromethyl-phenyl)-[1,2,4]oxadiazole | 102 | 100 |
| 3-[4-(1H-imidazol-1-ylmethyl)-2-(trifluoromethyl)phenyl]-5-(4-isopropoxy-3-methylphenyl)-1,2,4-oxadiazole | — | 7.4 |
| 3-[4-(1H-imidazol-1-ylmethyl)-2-(trifluoromethyl)phenyl]-5-[4-isopropoxy-3-(trifluoromethyl)phenyl]-1,2,4-oxadiazole | 62.4 | 80.9 |
| 3-[4-(1H-imidazol-1-ylmethyl)-2-(trifluoromethyl)phenyl]-5-(4-isopropoxy-3-nitrophenyl)-1,2,4-oxadiazole | 6.37 | 79.4 |
| 5-[3-bromo-4-(cyclopropyloxy)phenyl]-3-[4-(1H-imidazol-1-ylmethyl)-2-(trifluoromethyl)phenyl]-1,2,4-oxadiazole | 119 | 89.6 |
| 5-(3-bromo-4-isobutoxyphenyl)-3-[4-(1H-imidazol-1-ylmethyl)-2-(trifluoromethyl)phenyl]-1,2,4-oxadiazole | 144 | 98.3 |
| 5-{3-[2-chloro-4-(1H-imidazol-1-ylmethyl)phenyl]-1,2,4-oxadiazol-5-yl}-2-isopropoxybenzonitrile | 4.56 | 94.9 |
| 5-(3-bromo-4-isopropoxyphenyl)-3-[2-chloro-4-(1H-imidazol-1-ylmethyl)phenyl]-1,2,4-oxadiazole | 29.7 | 102 |
| 3-[2-chloro-4-(1H-imidazol-1-ylmethyl)phenyl]-5-[4-isopropoxy-3-(trifluoromethyl)phenyl]-1,2,4-oxadiazole; | 3.55 | 79.6 |
| 3-[2-chloro-4-(1H-imidazol-1-ylmethyl)phenyl]-5-(4-isopropoxy-3-nitrophenyl)-1,2,4-oxadiazole | 8.79 | 92.3 |
| 5-{3-[4-(1H-imidazol-1-ylmethyl)phenyl]-1,2,4-oxadiazol-5-yl}-2-(2-methylpiperidin-1-yl)benzonitrile | 130 | 99.9 |

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

Figure 1:
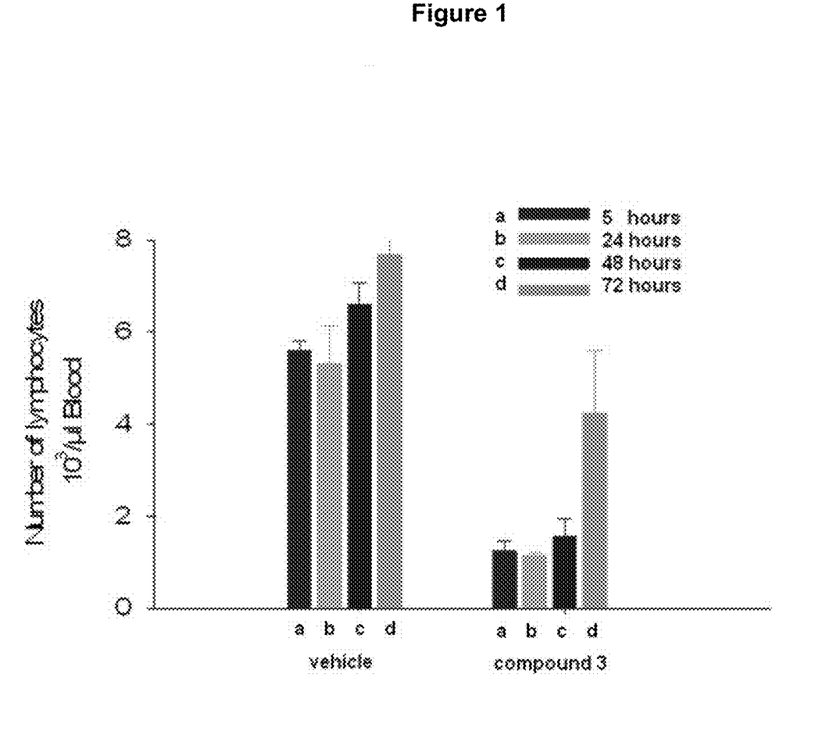
FIG. 1 shows the in vivo blood lymphocyte depletion after dosing the mice with Compound 3, 3-(4-Imidazol-1-ylm-ethyl-phenyl)-5-(4-isopropoxy-3-trifluoromethyl-phenyl)-[1,2,4]oxadiazole.
Figure 2:
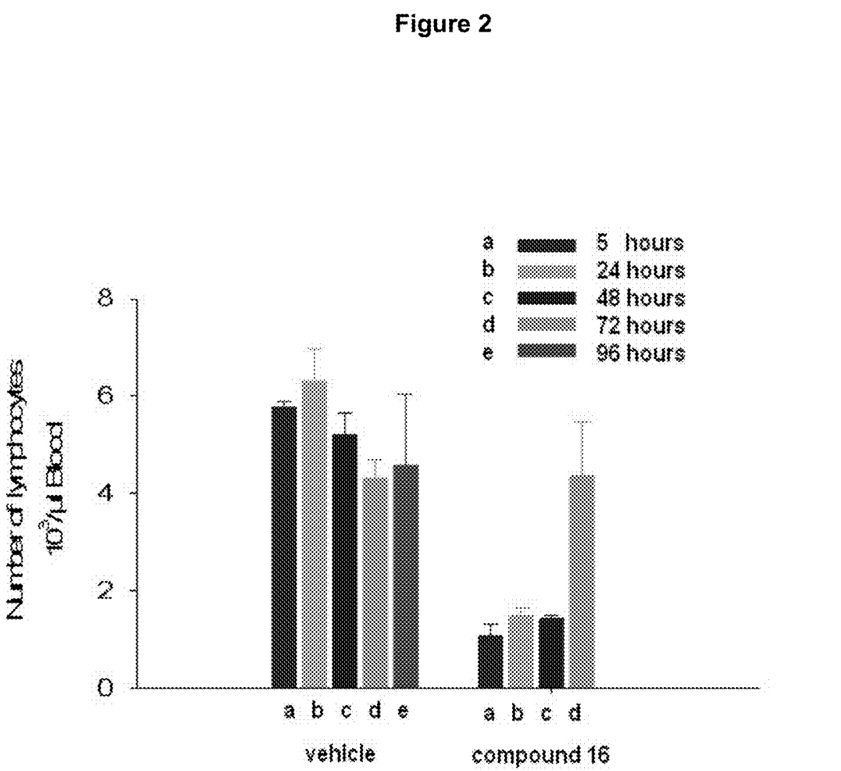
FIG. 2 shows the in vivo blood lymphocyte depletion after dosing the mice with Compound 16, 5-(3-Chloro-4-isopro-poxy-phenyl)-3-(4-imidazol-1-ylmethyl-phenyl)-[1,2,4] oxadiazole.

A lymphopenia assay in mice; as previously described, was employed to measure the in vivo blood lymphocyte depletion after dosing with 3-(4-Imidazol-1-ylmethyl-phenyl)-5-(4-isopropoxy-3-trifluoromethyl-phenyl)-[1,2,4]oxadiazole, Compound 3, (FIG. 1) and 5-(3-Chloro-4-isopropoxy-phenyl)-3-(4-imidazol-1-ylmethyl-phenyl)-[1,2,4]oxadiazole, Compound 16, (FIG. 2). These S1P agonist (or modulator) is useful for S1P-related diseases, and exemplified by the lymphopenia in vivo response. In general, test drugs Compound 3 and 16 were prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at 5, 24, 48, and 72 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in the following figures below that depict lowered lymphocyte count after 5 hours (<1 number of lymphocytes $10^3/\mu L$ blood).

What is claimed is:

1. A method of treating an immunosuppressant disorder associated with the sphingosine-1-phosphate receptor modulation, wherein the immunosuppressant disorder is selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant resection, in a mammal in need thereof, which comprises administering to a mammal in need thereof, a pharmaceutical composition comprising a therapeutically effective amount of at least one compound represented by Formula I or a pharmaceutically acceptable salt thereof:

Formula I wherein:

R is H, $C_{1-10}$ alkyl, $C_{3-10}$ cycloalkyl, —$OR^6$, $NR^7R^8$, halogen, nitrile, nitrogen dioxide, $C(O)R^9$, aryl or heterocycle;

$R^1$ is H, $C_{1-10}$ alkyl, $C_{3-10}$ cycloalkyl, —$OR^{10}$, $NR^{11}R^{12}$, halogen, nitrile, nitrogen dioxide, $C(O)R^{13}$, aryl or heterocycle;

$R^2$ is H, $C_{1-10}$ alkyl, halogen, aryl or heterocycle;

$R^3$ is $C_{1-10}$ alkyl, $C_{3-10}$ cycloalkyl, —$OR^{14}$, $NR^{15}R^{16}$, halogen, nitrile, nitrogen dioxide, $C(O)R^{17}$, aryl or heterocycle;

$R^4$ is $C_{1-10}$ alkyl, $C_{3-10}$ cycloalkyl, —$OR^{18}$, $NR^{19}R^{20}$, halogen, nitrile, nitrogen dioxide, $C(O)R^{21}$, aryl or heterocycle;

$R^5$ is $C_{1-10}$ alkyl, $C_{3-10}$ cycloalkyl, —$OR^{22}$, $NR^{23}R^{24}$, halogen, nitrile, nitrogen dioxide, $C(O)R^{25}$, aryl or heterocycle;

a is 0, 1, 2 or 3;

b is 0, 1, 2 or 3;

c is 0, 1, 2 or 3;

$R^6$ is H, $C_{3-10}$ cycloalkyl or $C_{1-10}$ alkyl;

R⁷ is H or C_{1-10} alkyl;
R⁸ is H or C_{1-10} alkyl;
R⁹ is H, C_{3-10} cycloalkyl, —OH, —OC_{3-10} cycloalkyl, —OC_{1-10} alkyl or C_{1-10} alkyl;
R¹⁰ is H, C_{3-10} cycloalkyl or C_{1-10} alkyl;
R¹¹ is H or C_{1-10} alkyl;
R¹² is H or C_{1-10} alkyl;
R¹³ is H, C_{3-10} cycloalkyl, —OH, —CO_{3-10} cycloalkyl, —OC_{1-10} alkyl or C_{1-10} alkyl;
R¹⁴ is H, C_{3-10} cycloalkyl or C_{1-10} alkyl;
R¹⁵ is H or C_{1-10} alkyl;
R¹⁶ is H or C_{1-10} alkyl;
R¹⁷ is H, C_{3-10} cycloalkyl, —OH, —CO_{3-10} cycloalkyl, —OC_{1-10} alkyl or C_{1-10} alkyl;
R¹⁸ is H, C_{3-10} cycloalkyl or C_{1-10} alkyl;
R¹⁹ is H or C_{1-10} alkyl;
R²⁰ is H or C_{1-10} alkyl;
R²¹ is H, C_{3-10} cycloalkyl, —OH, —CO_{3-10} cycloalkyl, —OC_{1-10} alkyl or C_{1-10} alkyl;
R²² is H, C_{3-10} cycloalkyl or C_{1-10} alkyl;
R²³ is H or C_{1-10} alkyl;
R²⁴ is H or C_{1-10} alkyl; and
R²⁵ is H, C_{3-10} cycloalkyl, —OH, —CO_{3-10} cycloalkyl, —OC_{1-10} alkyl or C_{1-10} alkyl.

2. The method according to claim 1, wherein said compound is represented by Formula I wherein:
R is H, nitrile, C_{1-10} alkyl, halogen or nitrogen dioxide; and
R¹ is C_{1-10} alkyl, OR¹⁰, or heterocycle; and
R² is H, halogen or C_{1-10} alkyl; and
a is 0; and
b is 0; and
c is 0; and
R¹⁰ is isopropyl, isobutyl, cyclohexyl or cyclopropyl.

3. The method according to claim 1, wherein said compound is represented by Formula I wherein:
R is H, nitrile, bromine, trifluoromethyl, nitrogen dioxide, methyl or chlorine; and
R¹ is isopropoxy, cyclopropoxy, isobutoxy or 2-methylpiperidin-1-yl; and
R² is H, methyl, trifluoromethyl or chlorine; and
a is 0; and
b is 0; and
c is 0; and
R¹⁰ is isopropyl or cyclopropyl.

4. The method according to claim 1, wherein the mammal is a human.

5. The method according to claim 1, wherein the pharmaceutical composition further comprises pharmaceutically acceptable adjuvants, diluents or carriers.

6. The method according to claim 1, wherein the compound represented by Formula I is selected from:
3-(4-Imidazol-1-ylmethyl-phenyl)-5-(4-isobutyl-phenyl)-[1,2,4]oxadiazole;
5-[3-(4-Imidazol-1-ylmethyl-phenyl)-[1,2,4]oxadiazol-5-yl]-2-isopropoxy-benzonitrile;
3-(4-Imidazol-1-ylmethyl-phenyl)-5-(4-isobutoxy-3-trifluoromethyl-phenyl)-[1,2,4]oxadiazole;
5-(4-Cyclohexyloxy-3-trifluoromethyl-phenyl)-3-(4-imidazol-1-ylmethyl-phenyl)-[1,2,4]oxadiazole;
3-(4-Imidazol-1-ylmethyl-phenyl)-5-(4-isopropoxy-3-trifluoromethyl-phenyl)-[1,2,4]oxadiazole;
5-(3-Chloro-4-isopropoxy-phenyl)-3-(4-imidazol-1-ylmethyl-phenyl)-[1,2,4]oxadiazole;
5-(3-Bromo-4-isopropoxy-phenyl)-3-(4-imidazol-1-ylmethyl-phenyl)-[1,2,4]oxadiazole;
5-[3-(4-Imidazol-1-ylmethyl-phenyl)-[1,2,4]oxadiazol-5-yl]-2-isobutoxy-benzonitrile;
3-(4-Imidazol-1-ylmethyl-phenyl)-5-(4-isopropoxy-phenyl)-[1,2,4]oxadiazole;
3-(4-Imidazol-1-ylmethyl-phenyl)-5-(4-isopropoxy-3-methyl-phenyl)-[1,2,4]oxadiazole;
3-(4-Imidazol-1-ylmethyl-phenyl)-5-(4-isopropoxy-3-nitro-phenyl)-[1,2,4]oxadiazole;
5-(3-Bromo-4-isobutoxy-phenyl)-3-(4-imidazol-1-ylmethyl-phenyl)-[1,2,4]oxadiazole;
5-[3-(4-Imidazol-1-ylmethyl-2-methyl-phenyl)-[1,2,4]oxadiazol-5-yl]-2-isopropoxy-benzonitrile;
3-(4-Imidazol-1-ylmethyl-2-methyl-phenyl)-5-(4-isopropoxy-3-nitro-phenyl)-[1,2,4]oxadiazole;
5-(3-Bromo-4-isopropoxy-phenyl)-3-(4-imidazol-1-ylmethyl-2-methyl-phenyl)-[1,2,4]oxadiazole;
5-(3-Bromo-4-cyclopropoxy-phenyl)-3-(4-imidazol-1-ylmethyl-phenyl)-[1,2,4]oxadiazole;
5-(3-Bromo-4-cyclopropoxy-phenyl)-3-(4-imidazol-1-ylmethyl-2-methyl-phenyl)-[1,2,4]oxadiazole;
3-(4-Imidazol-1-ylmethyl-2-methyl-phenyl)-5-(4-isopropoxy-3-trifluoromethyl-phenyl)-[1,2,4]oxadiazole;
3-(4-Imidazol-1-ylmethyl-2-methyl-phenyl)-5-(4-isopropoxy-3-methyl-phenyl)-[1,2,4]oxadiazole;
5-[3-(4-Imidazol-1-ylmethyl-2-trifluoromethyl-phenyl)-[1,2,4]oxadiazol-5-yl]-2-isopropoxy-benzonitrile;
5-(3-Bromo-4-isopropoxy-phenyl)-3-(4-imidazol-1-ylmethyl-2-trifluoromethyl-phenyl)-[1,2,4]oxadiazole;
3-[4-(1H-imidazol-1-ylmethyl)-2-(trifluoromethyl)phenyl]-5-(4-isopropoxy-3-methylphenyl)-1,2,4-oxadiazole;
3-[4-(1H-imidazol-1-ylmethyl)-2-(trifluoromethyl)phenyl]-5-[4-isopropoxy-3-(trifluoromethyl)phenyl]-1,2,4-oxadiazole;
3-[4-(1H-imidazol-1-ylmethyl)-2-(trifluoromethyl)phenyl]-5-(4-isopropoxy-3-nitrophenyl)-1,2,4-oxadiazole;
5-[3-bromo-4-(cyclopropyloxy)phenyl]-3-[4-(1H-imidazol-1-ylmethyl)-2-(trifluoromethyl)phenyl]-1,2,4-oxadiazole;
5-(3-bromo-4-isobutoxyphenyl)-3-[4-(1H-imidazol-1-ylmethyl)-2-(trifluoromethyl)phenyl]-1,2,4-oxadiazole;
5-{3-[2-chloro-4-(1H-imidazol-1-ylmethyl)phenyl]-1,2,4-oxadiazol-5-yl}-2-isopropoxybenzonitrile;
5-(3-bromo-4-isopropoxyphenyl)-3-[2-chloro-4-(1H-imidazol-1-ylmethyl)phenyl]-1,2,4-oxadiazole;
3-[2-chloro-4-(1H-imidazol-1-ylmethyl)phenyl]-5-[4-isopropoxy-3-(trifluoromethyl)phenyl]-1,2,4-oxadiazole;
3-[2-chloro-4-(1H-imidazol-1-ylmethyl)phenyl]-5-(4-isopropoxy-3-nitrophenyl)-1,2,4-oxadiazole; and
5-{3-[4-(1H-imidazol-1-ylmethyl)]-1,2,4-oxadiazol-5-yl}-2-(2-methylpiperidin-1-yl)benzonitrile.

7. The method according to claim 1, wherein the compound represented by Formula I is 3-(4-Imidazol-1-ylmethyl-phenyl)-5-(4-isopropoxy-3-trifluoromethyl-phenyl)-[1,2,4]oxadiazole, or a pharmaceutically acceptable salt thereof.

8. The method according to claim 1, wherein the compound represented by Formula I is 5-(3-Chloro-4-isopropoxy-phenyl)-3-(4-imidazol-1-ylmethyl-phenyl)-[1,2,4]oxadiazole, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,440,698 B2 | |
| APPLICATION NO. | : 13/567654 | |
| DATED | : May 14, 2013 | |
| INVENTOR(S) | : Takeuchi et al. | |

It is certified that error appears in the above-identified patent and that said Letters Patent is hereby corrected as shown below:

On the title page, item (56), under "Other Publications", in column 2, line 2, delete "Joumal" and insert -- Journal --, therefor.

On the title page, item (56), under "Other Publications", in column 2, line 12, delete "0xadiazole" and insert -- Oxadiazole --, therefor.

On the title page, item (56), under "Other Publications", in column 2, line 14, delete "Florian6polis," and insert -- Florianopolis, --, therefor.

On the title page, item (56), under "Other Publications", in column 2, line 20, delete "Scient," and insert -- Science, --, therefor.

In the Specification

In column 1, line 54, delete "sphingomyeline" and insert -- sphingomyelin --, therefor.

In column 3, line 47, delete "$O_{1-10}$" and insert -- $C_{1-10}$ --, therefor.

In column 3, line 47, delete "$O_{3-10}$" and insert -- $C_{3-10}$ --, therefor.

In column 5, line 34, delete "methylpiperdin" and insert -- methylpiperidin --, therefor.

In column 6, lines 22-23, delete "methylpiperdin" and insert -- methylpiperidin --, therefor.

In column 8, line 19, delete "Stahal" and insert -- Stahl --, therefor.

In column 8, line 20, delete "Chemica" and insert -- Chimica --, therefor.

In column 9, line 2, delete "antoimmune" and insert -- autoimmune --, therefor.

In column 9, line 3, delete "dermititis," and insert -- dermatitis, --, therefor.

In column 9, lines 50-51, delete "antoimmune" and insert -- autoimmune --, therefor.

In column 9, line 52, delete "dermititis," and insert -- dermatitis, --, therefor.

In column 13, line 29, delete "diasteroisomeric" and insert -- diastereoisomeric --, therefor.

In column 13, line 58, delete "CU" and insert -- CDI --, therefor.

Signed and Sealed this
Eighth Day of October, 2013

Teresa Stanek Rea
*Deputy Director of the United States Patent and Trademark Office*

CERTIFICATE OF CORRECTION (continued)
U.S. Pat. No. 8,440,698 B2

In column 13, line 65, delete "CLCH$_2$L" and insert -- CLCH$_2$I --, therefor.

In column 15, line 24, delete "CU" and insert -- CDI --, therefor.

In column 18, lines 2-3, delete "recrystalization" and insert -- recrystallization --, therefor.

In column 18, line 41 (Table 2), delete "Intremediate" and insert -- Intermediate --, therefor.

In column 18, line 57 (Table 2), delete "Intremediate" and insert -- Intermediate --, therefor.

In column 19, line 46, delete "dithitothreitol" and insert -- dithiothreitol --, therefor.

In column 19, line 51, delete "adenylylimmidodiphosphate" and insert
-- adenylylimidodiphosphate --, therefor.

In column 21, line 47 (Table), delete "1,2,4-oxadiazole;" and insert -- 1,2,4-oxadiazole --, therefor.

In the Claims

In column 22, line 30, in claim 1, delete "resection," and insert -- rejection, --, therefor.

In column 23, line 8, in claim 1, delete "CO$_{3-10}$" and insert -- OC$_{3-10}$ --, therefor.

In column 23, line 13, in claim 1, delete "CO$_{3-10}$" and insert -- OC$_{3-10}$ --, therefor.

In column 23, line 18, in claim 1, delete "CO$_{3-10}$" and insert -- OC$_{3-10}$ --, therefor.

In column 23, line 23, in claim 1, delete "CO$_{3-10}$" and insert -- OC$_{3-10}$ --, therefor.